United States Patent [19]

Clayton

[11] Patent Number: 4,898,709
[45] Date of Patent: Feb. 6, 1990

[54] ORE IRRADIATOR

[75] Inventor: Colin G. Clayton, Abingdon, England

[73] Assignee: United Kingdom Atomic Energy Authority, London, England

[21] Appl. No.: 75,213

[22] Filed: Jul. 20, 1987

Related U.S. Application Data

[63] Continuation of Ser. No. 678,565, filed as PCT GB84/00132 on Apr. 18, 1984, published as WO84/04393 on Nov. 8, 1984, abandoned.

[30] Foreign Application Priority Data

Apr. 22, 1983 [GB] United Kingdom ................ 8310991

[51] Int. Cl.⁴ .............................................. G21G 1/06
[52] U.S. Cl. .................................. 376/159; 376/194; 376/202
[58] Field of Search ................ 376/151, 157, 159, 202, 376/114, 115, 194, 340, 342

[56] References Cited

U.S. PATENT DOCUMENTS 2,816,242 12/1957 Goodman .......................... 376/194
3,325,371 6/1967 Stanton ............................. 376/193
3,400,290 9/1968 Bergan ............................ 376/151
3,911,282 10/1975 Bergan ............................ 376/151

FOREIGN PATENT DOCUMENTS 861316 2/1961 United Kingdom ................ 376/323
2055465 3/1981 United Kingdom .
2101304 1/1983 United Kingdom .

OTHER PUBLICATIONS

Kern Technik, Vol. 17, No. 1, 1975, pp. 36–41.

Primary Examiner—Harvey E. Behrend
Attorney, Agent, or Firm—William R. Hinds

[57] ABSTRACT

An irradiator (4) is provided for irradiating lumps of ore to detect the presence of gold in the lumps by neutron activation analysis. The irradiator (4) consists of a close packed array of three inner cylindrical ducts (14) and three outer cylindrical ducts (12) through which the lumps of ore are passed, with three neutron sources (16) arranged in the spaces between the inner ducts (14) and the outer ducts (12) to irradiate the ducts (12, 14) and to activate any gold by the reaction $^{197}$Au (n, n'$\gamma$) $^{197}$Au. Each inner duct (14) is thus adjacent to two neutron sources (16), and is or larger cross-sectional area than the outer ducts (12).

15 Claims, 2 Drawing Sheets

ORE IRRADIATOR

This application is a continuation of application Ser. No. 678,565, filed as PCT GB84/00132 on Apr. 18, 1984, published as WO84/04393 on Nov. 8, 1984, now abandoned.

This invention relates to apparatus for detecting the presence of a selected substance in ores by neutron activation analysis, for example the gold content of gold-bearing ores.

A practical gold ore sorting plant needs to be able to process several tonnes of ore an hour, and hence must use a rapid analytical technique. A suitable technique is neutron activation analysis using the reaction $^{197}$Au (n, n'$\gamma$) $^{197m}$Au to activate gold present in a lump of ore, the $^{197m}$Au nuclides so produced decaying with a half-life of about 7.8 seconds, with the emission of $\gamma$-rays of energy 279 keV. British Patent Specifications Nos. 2 055 465A and 2 101 304A (U.S. Pat. No. 4 340 443, and U.S. Ser. No. 383 686 filed 27 May 1982, respectively) which are incorporated by reference herein, describe apparatus for sorting gold bearing ores in which lumps of ore are activated by the above reaction, the $\gamma$-rays emitted subsequently being detected and analysed to assess the gold content of the ores.

According to the present invention there is provided an irradiator for irradiating lumps of ore for detecting the presence of a selected substance in the lumps, the irradiator comprising a plurality of ducts arranged in a close-packed array, means for rotating each duct about its longitudinal axis, and a plurality of neutron sources for irradiating the ducts and located in spaces between the ducts so that each duct is adjacent to at least one source.

Preferably, the ducts are arranged to be upright in use. Each neutron source may comprise a target arranged to be bombarded by a high energy particle beam, the particle beams being incident on the targets in a direction parallel to the longitudinal axes of the ducts and provided by a common particle accelerator.

Some of the ducts are desirably adjacent to and thereby irradiated by more than one neutron source, and these ducts may be of greater cross-sectional area than those ducts which are adjacent to only one neutron source.

Conveniently, the number of ducts is six and the number of neutron sources three, and the longitudinal axes of the ducts may be located approximately at the vertices of an equilateral triangle and at the mid-points of the sides of the triangle.

In the preferred embodiment of the invention for detecting the presence of gold in gold-bearing ores, each neutron source comprises a lithium target arranged to be bombarded by a beam of high energy protons so as to produce neutrons of energy between 0.5 and 3.0 MeV.

The invention will now be further described by way of example only and with reference to the accompanying drawings, in which.

Figure 1:
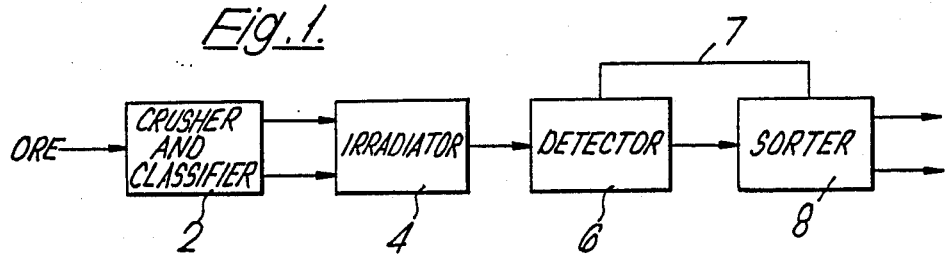
FIG. 1 is a flow diagram of a gold ore sorting apparatus including an irradiator according to the invention.

Referring to FIG. 1, a gold ore sorting apparatus comprises a rock crusher and classifier 2 to which mined ore is supplied, in which the ore is crushed into lumps and divided into two streams of lumps corresponding to mesh sizes of about 80 mm and 60 mm respectively, while lumps smaller than mesh size about 35 mm are rejected. Both streams of lumps are passed through an irradiator 4 to be described in more detail later, and then all the lumps are caused to pass a $\gamma$-ray detector assembly 6 arranged to detect $\gamma$-rays having an energy of 279 keV arising from the decay of $^{197m}$Au nuclides and so signifying the presence of gold in the lumps of ore. Each lump of ore is interrogated individually by the detector assembly 6 to establish whether its gold content lies above or below some predetermined concentration. The critical concentration is typically in the range 0.5 to 5 parts per million (ppm), and might for example be set at 1 ppm. Each lump of ore is then passed into a sorter 8 arranged by means of a cable 7 to respond to signals from the detector assembly 6, and to sort each lump of ore into one of two outlet streams depending on whether the gold concentration in the lump lies above or below the predetermned concentration.

The crusher and classifier 2 and the sorter 8 may be of types well known in the art, while the detector assembly 6 may be as described more fully in the aforementioned specifications to which reference may be made, the crusher and classifier 2, the sorter 8 and the detector assembly 6 not being the subject of the invention.

Figure 2:
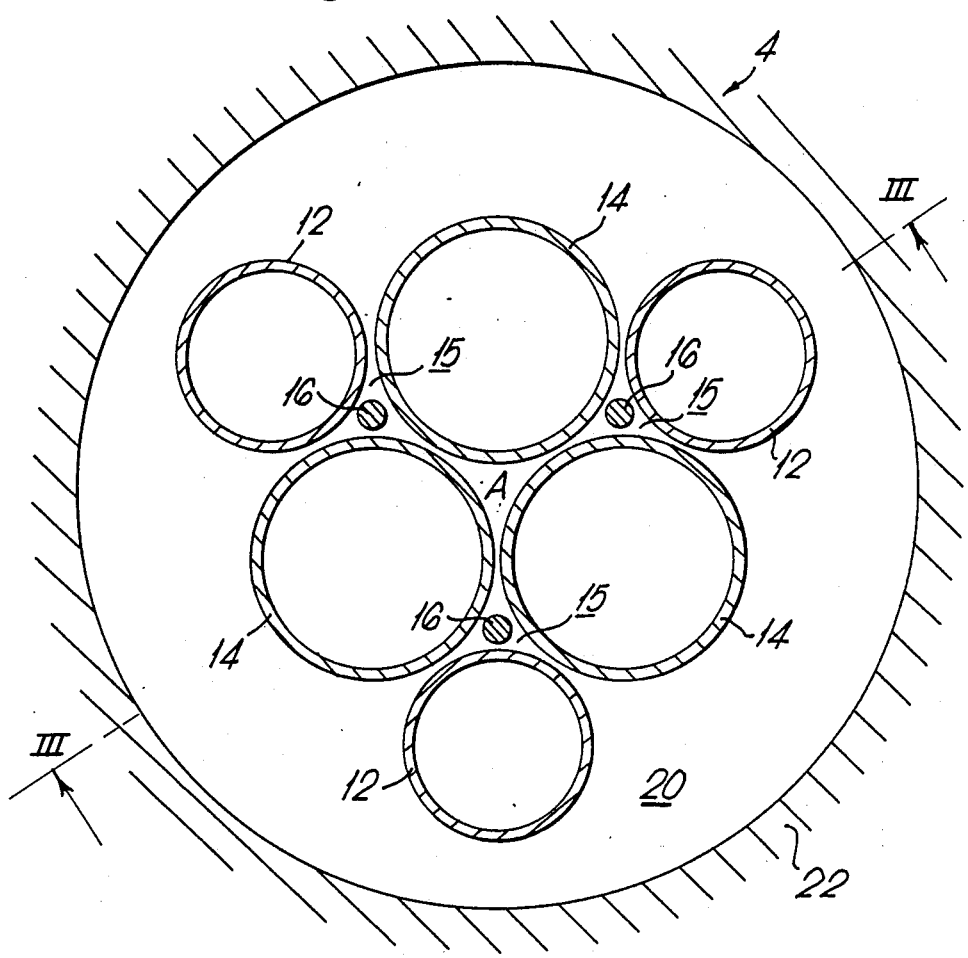
FIG. 2 is a cross-sectional representation of the irradiator of FIG. 1.
Figure 3:
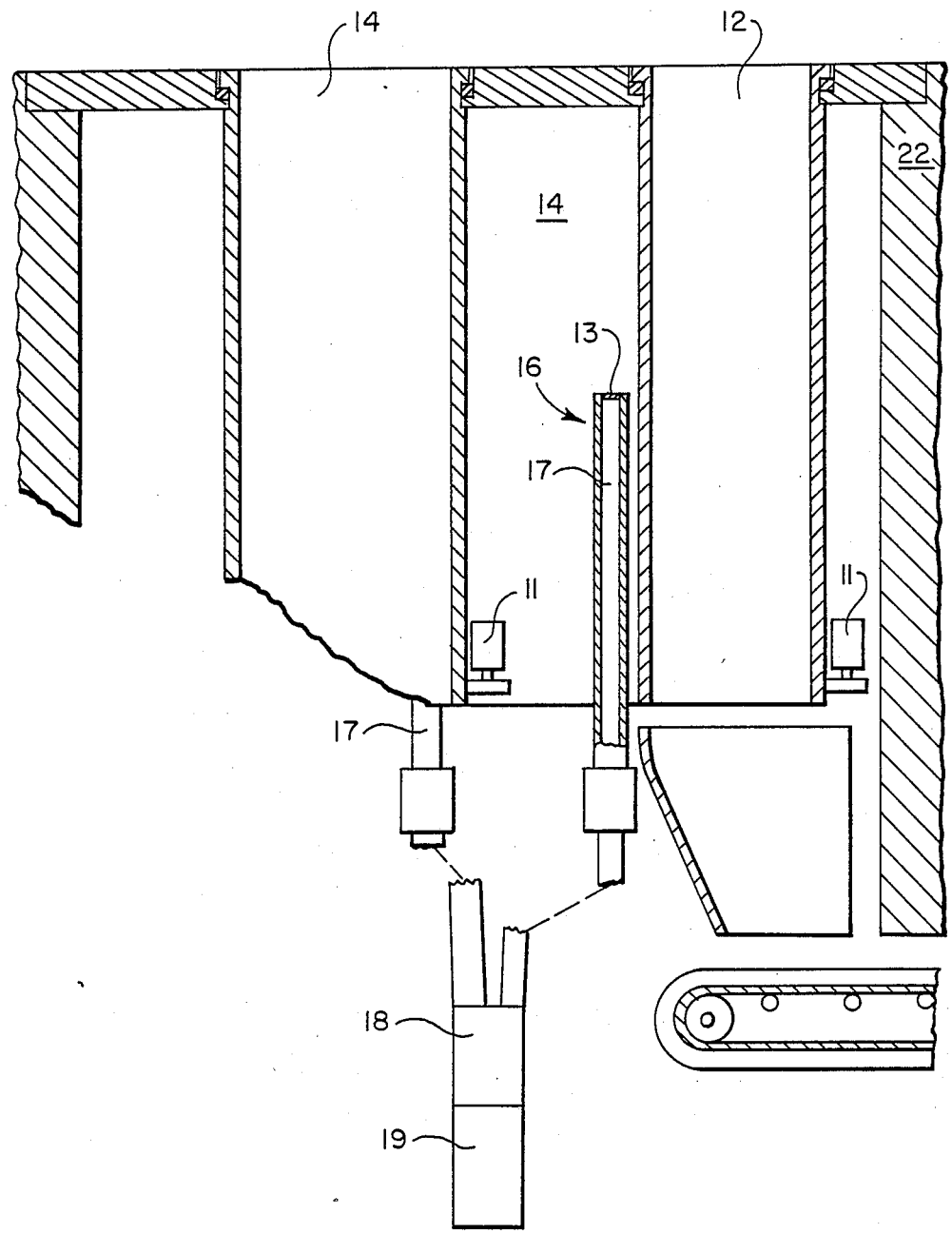
FIG. 3 shows a view on the line III—III of FIG. 2.

Referring to FIG. 2 and FIG. 3, the irradiator 4 comprises a close packed array of three outer tubular steel cylinders 12 and three inner tubular steel cylinders 14, with their longitudinal axes upright, the axes of the three outer cylinders 12 being at the corners of a notational equilateral triangle, and the axes of the three inner cylinders 14 being near the mid points of the sides of the triangle. Each of the inner cylinders 14 is of internal diameter 32 cm and each of the outer cylinders 12 is of internal diameter 26 cm. The outer cylinders 12 and the inner cylinders 14, although close packed, are not contiguous, and each is caused to rotate about its longitudinal axis in a clockwise sense by a drive from an electric motor 11.

The outer cylinders 12 and the inner cylinders 14 adjacent thereto define between them three spaces 15 in which respective neutron sources 16 are situated in a horizontal plane at an intermediate position along the length of the outer cylinders 12 and the inner cylinders 14. Each neutron source 16 comprises a lithium target 13, at the end of a respective evacuated flight tube 17, the three flight tubes 17 emerging via a beam splitter 18 from a single proton accelerator 19, and the end portion of each flight tube 17 extending parallel to the axes of the cylinders 12, 14. Flight tubes, beam splitters and accelerators are well known in the art, and further details will not be given.

The outer cylinders 12, the inner cylinders 14 and the neutron sources 16 are located within a cylindrical chamber 20 defined by a concrete radiation shield 22 which is sufficiently thick to be substantially impervious to $\gamma$-rays and to neutrons and far enough away so as not to generate an intense field of interfering low energy neutrons. A typical distance is 100 cm.

In operation of the irradiator 4, the streams of ore from the crusher and classifier 2 (see FIG. 1) are passed through the outer cylinders 12 and the inner cylinders 14, the stream of larger lumps of ore being passed through the inner cylinders 14. The accelerator is energised to cause a beam of protons of energy 4.5 MeV to bombard each lithium target, the proton beam being moved around the surface of the target to avoid localized overheating. Fast neutrons of energy between about 0.5 MeV and 2.8 MeV are produced by the reaction

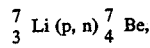

and irradiate the lumps of ore in the adjacent outer cylinders 12 and inner cylinders 14. The neutron flux decreases with distance from the sources 16, hence to provide as uniform an irradiation of the ore lumps as possible the outer cylinders 12 and the inner cylinders 14 are rotated about their respective longitudinal axes so that each lump of ore traverses the high intensity region of the neutron flux from one of the sources 16 twice, as it passes along the cylinder 12, 14.

If any gold is present in a lump of ore it will be activated by the reaction $^{197}$Au (n, n'γ) $^{197m}$Au the cross-section for which is a maximum for neutrons of energy about 2.5 MeV. Fast neutrons of energy below 2.8 MeV are capable of bringing about this activation, but have insufficient energy to bring about activation by (n, p) reactions of other elements which are likely to be present in the ore, such as aluminium and silicon.

The irradiator 4 enables a greater throughput of ore to be irradiated than the irradiators described in the aforementioned specifications and also enables larger lumps of ore to be irradiated. This is because each of the sources 16 can produce a total neutron flux of about $10^{12}$ neutrons/second, about ten times greater than the neutron fluxes available from the sources described in the aforementioned specifications, and because the use of two sources 16 to irradiate each of the larger, inner cylinders 14 means that substantially uniform irradiation and activation of all the lumps of ore in each inner cylinder 14 is achievable with cylinders of larger diameter than can be satisfactorily irradiated with a single neutron source.

It will be appreciated that the uniformity of irradiation of lumps of ore in the three inner cylinders 14 may be still further improved by the provision of a fourth neutron source at the position marked A in FIG. 2 between the three inner cylinders 14.

The inner cylinders 14 and the outer cylinders 12 may have diameters differing from the values given. However to avoid interfering excitations brought about by intermediate energy neutrons all the cylinders are preferably of diameter less than about 50 cm, while to ensure uniform irradiation of the lumps of ore those cylinders which are adjacent to only one neutron source are preferably of diameter less than 35 cm. It will also be appreciated that the number of cylinders need not be six, and that they may be disposed in a different close-packed array.

It will be understood that although the sources 16 have been described as comprising lithium targets onto which generally vertical beams of protons are incident from a common accelerator, each target may be bombarded by a particle beam from a separate accelerator. It will also be understood that alternative neutron sources such as those utilizing a D (D, n) $^3$He reaction may be used as long as the neutrons produced are of energies less than about 3 MeV.

I claim:

1. An irradiator for irradiating lumps of ore for detecting the presence of a selected substance in the lumps, the irradiator comprising a plurality of cylindrical ducts (12, 14) through which, in operation, lumps of ore are caused to pass, and means for rotating each duct about its longitudinal axis, characterised in that the ducts are arranged in a close-packed array so as to define roughly triangular spaces (15) between the ducts, each said space being defined by walls of three adjacent ducts, with clearance between neighboring ducts sufficient to allow rotation of the ducts, and that a plurality of neutron sources (16) for irradiating the ducts are provided, at least some of the roughly triangular spaces between the ducts having a said neutron source therein so that each duct is adjacent to at least one source, some of the ducts being adjacent to, and so in use irradiated by, more than one neutron source, the other ducts being adjacent to one source, the former ducts being of greater cross-sectional area than the latter, each source comprising a target, and means to generate a high energy particle beam incident onto the target in a direction substantially parallel to the longitudinal axes of the ducts, and of such an energy that in operation neutrons bring about excitation of atoms of the selected substance in the lumps.

2. An irradiator as claimed in claim 1 wherein the ducts (12, 14) are arranged to be upright in use, so that gravity causes the lumps to move down the ducts.

3. An irradiator as claimed in claim 1 comprising a particle accelerator, and a plurality of beam tubes extending substantially parallel to the longitudinal axes of the ducts to carry the particle beams from the particle generator to the targets.

4. An irradiator as claimed in claim 1 wherein the number of ducts is six and the longitudinal axes of the ducts are located at least approximately at the vertices of an equilateral triangle and at the mid-points of the sides of the triangle, and the irradiator includes three neutron sources.

5. An irradiator as claimed in claim 1 also including a radiation shield (22) surrounding the ducts and spaced away from them.

6. An irradiator as claimed in claim 1 wherein the ducts are of width about 30 cm.

7. An irradiator as claimed in claim 1, suitable for detecting the presence of gold in gold-bearing ores, wherein the target is of lithium and the particle beam is of high energy protons of such an energy as to produce neutrons of energy between 0.5 and 3.0 MeV.

8. An ore sorting apparatus incorporating an irradiator as claimed in claim 1.

9. An ore sorting apparaus incorporating an irradiator as claimed in claim 2.

10. An ore sorting apparatus incorporating an irradiator as claimed in claim 3.

11. An ore sorting apparatus incorporating an irradiator as claimed in claim 4.

12. An ore sorting apparatus incorporating an irradiator as claimed in claim 5.

13. An ore sorting apparatus incorporating an irradiator as claimed in claim 6.

14. An ore sorting apparatus incorporating an irradiator as claimed in claim 7.

15. An irradiator as claimed in claim 4 wherein each neutron source is located in a separte space defined between one duct located approximately at a vertex of the triangle and two ducts located approximately at midpoints of two sides of the triangle, and wherein said side-located ducts are of diameter greater than said vertex-located ducts.

* * * * *